(12) United States Patent
Knollman et al.

(10) Patent No.: US 12,357,805 B2
(45) Date of Patent: Jul. 15, 2025

(54) COMPOSITIONS, DISPENSERS, AND METHODS THEREOF FOR ESTABLISHING A URINE PASSAGEWAY THROUGH A URETER

(71) Applicant: Bard Peripheral Vascular, Inc., Franklin Lakes, NJ (US)

(72) Inventors: Kevin Knollman, West Chester, OH (US); Christopher Bowley, Newport, RI (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 820 days.

(21) Appl. No.: 17/459,845

(22) Filed: Aug. 27, 2021

(65) Prior Publication Data
US 2022/0062609 A1    Mar. 3, 2022

Related U.S. Application Data

(60) Provisional application No. 63/071,872, filed on Aug. 28, 2020.

(51) Int. Cl.
*A61M 37/00* (2006.01)
*A61B 1/307* (2006.01)
(Continued)

(52) U.S. Cl.
CPC ......... *A61M 37/0069* (2013.01); *A61B 1/307* (2013.01); *A61B 90/37* (2016.02);
(Continued)

(58) Field of Classification Search
None
See application file for complete search history.

(56) References Cited

U.S. PATENT DOCUMENTS 9,173,735 B2   11/2015 Davoudi et al.
2007/0088252 A1*  4/2007 Pestotnik .......... B01F 35/75425
                                                 604/82
(Continued)

OTHER PUBLICATIONS

Wang, X., Shan, H., Wang, J., Hou, Y., Ding, J., Chen, Q., Guan, J., Wang, C., & Chen, X. (2015), Characterization of nanostructured ureteral stent with gradient degradation in a porcine model. Int. J. Nanomed. 10, 3055-3064.

(Continued)

*Primary Examiner* — Susan S Su
*Assistant Examiner* — Katherine-Ph Minh Pham
(74) *Attorney, Agent, or Firm* — Rutan & Tucker LLP

(57) ABSTRACT

Disclosed are compositions, dispensers, and methods thereof for establishing a urine passageway through a ureter. For example, a composition can include, in some embodiments, a primary solid phase and a secondary solid phase. The primary solid phase can include a monomer, a prepolymer, or a mixture thereof configured to commence polymerization into a polymeric form in the ureter when contacted with a fluid such as urine or saline. The secondary solid phase is dispersed in the primary solid phase. The secondary solid phase can include a leachable component. The leachable component is configured to leach from the polymeric form when contacted with a sufficient amount of a same or different fluid. The leachable component is also configured to form pores of an open-pore network throughout the polymeric form when leached from the polymeric form, thereby establishing the urine passageway through the ureter.

13 Claims, 6 Drawing Sheets

(51) Int. Cl.
*A61B 90/00* (2016.01)
*A61M 25/00* (2006.01)
*A61M 27/00* (2006.01)
*A61M 39/22* (2006.01)

(52) U.S. Cl.
CPC ...... *A61M 25/0017* (2013.01); *A61M 25/002* (2013.01); *A61M 27/002* (2013.01); *A61M 39/223* (2013.01); A61B 2090/376 (2016.02); A61M 2202/064 (2013.01); A61M 2205/32 (2013.01); A61M 2210/1082 (2013.01); A61M 2210/1089 (2013.01)

(56) References Cited

U.S. PATENT DOCUMENTS

| | | | |
|---|---|---|---|
| 2009/0164013 A1* | 6/2009 | Cruise | A61B 90/39 523/115 |
| 2016/0074602 A1* | 3/2016 | Wang | A61M 15/0003 604/518 |
| 2016/0120528 A1* | 5/2016 | Abtin | A61L 24/0015 604/91 |
| 2019/0000667 A1* | 1/2019 | Dollberg | A61F 7/12 |

OTHER PUBLICATIONS

Zhang, M.Q., Zou, T., Huang, Y.C., Shang, Y.F., Yang, G.G., Wang, W.Z., Zhou, J.M., Wang, L., Chen, F. and Xie, H. (2014), Evaluation of a novel ureteral stent. Int. J. Urol. 21: 401-407.

\* cited by examiner

COMPOSITIONS, DISPENSERS, AND METHODS THEREOF FOR ESTABLISHING A URINE PASSAGEWAY THROUGH A URETER

PRIORITY

This application claims the benefit of priority to U.S. Provisional Patent Application No. 63/071,872, filed Aug. 28, 2020, which is incorporated by reference in its entirety into this application.

BACKGROUND

At the end of a kidney-stone surgical procedure by way of, for example, ureteroscopy or percutaneous nephrolithotomy ("PCNL"), a ureteral stent is commonly placed in the ureter in order to maintain a urine passageway from the kidney to the bladder. (See FIG. 6 for an illustration of such a ureteral stent in a portion of a urinary system.) As shown in FIG. 6, one pigtail of the ureteral stent is placed in the kidney, and the other pigtail is placed in the bladder, which prevents migration of the ureteral stent. Such a ureteral stent is typically left in place for about 2-4 weeks while the patient heals from the surgical procedure.

One major issue with existing ureteral stents is patient discomfort or pain during the indwelling period thereof. While the mechanism of the discomfort or pain is not fully understood, it is thought that a pigtail of a ureteral stent disposed in the bladder might be a significant contributor of bladder-wall irritation. As shown in FIG. 6, a pigtail of a ureteral stent disposed in the bladder also forces open the anatomical one-way valve across the ureterovesicular junction, which possibly allows urine to reflux from the bladder back into the ureter or kidney. A third possible contributor of the discomfort or pain during the indwelling period is ureteral-stent interruption of the peristaltic muscular action of the smooth muscle of the ureter that moves urine into the bladder. (See peristatic action or lack thereof in FIGS. 5 and 6.)

Disclosed herein are compositions, dispensers, and methods thereof for establishing a urine passageway from a kidney to a bladder through a ureter.

SUMMARY

Disclosed herein is a composition for establishing a urine passageway through a ureter. The composition includes, in some embodiments, a primary solid phase and a secondary solid phase. The primary solid phase includes a monomer, a pre-polymer, or a mixture thereof configured to commence polymerization into a polymeric form in the ureter when contacted with a fluid. The secondary solid phase is dispersed in the primary solid phase. The secondary solid phase includes a leachable component. The leachable component is configured to leach from the polymeric form when contacted with a sufficient amount of a same or different fluid. The leachable component is also configured to form pores of an open-pore network throughout the polymeric form when leached from the polymeric form, thereby establishing the urine passageway through the ureter.

In some embodiments, the composition further includes a tertiary solid phase dispersed in the primary solid phase of the composition. The tertiary solid phase includes a radiopaque material configured to occupy interstices of the polymeric form upon polymerization thereof, thereby conferring radiopacity to the polymeric form.

In some embodiments, the leachable component is a salt or a sugar.

In some embodiments, the composition is a free-flowing powder configured to be infused into the ureter through a working channel of a ureteroscope or a lumen of an open-ended ureteral catheter.

In some embodiments, the composition is configured to adhere to urothelial tissue.

In some embodiments, the polymeric form is configured to bioabsorb over a period of time commensurate with an amount of the composition disposed in the ureter.

In some embodiments, the polymeric form is configured to degrade in urine and flush from a urinary system over a period of time commensurate with an amount of the composition disposed in the ureter.

Also disclosed is a packaged composition for establishing a urine passageway through a ureter. The packaged composition includes, in some embodiments, a dispenser including the composition. The dispenser includes a bellows coupled to a flanged hub having a Luer-tapered nozzle. The composition is disposed in the bellows. The composition includes a primary solid phase and a secondary solid phase. The primary solid phase includes a monomer, a pre-polymer, or a mixture thereof configured to commence polymerization into a polymeric form in the ureter when contacted with a fluid. The secondary solid phase is dispersed in the primary solid phase. The secondary solid phase includes a leachable component. The leachable component is configured to leach from the polymeric form when contacted with a sufficient amount of a same or different fluid. The leachable component is also configured to form pores of an open-pore network throughout the polymeric form when leached from the polymeric form, thereby establishing the urine passageway through the ureter.

In some embodiments, the dispenser further includes a valve fluidly connected to the bellows. The valve is configured to open and provide air to the bellows when the bellows are allowed to return to an equilibrium state thereof.

In some embodiments, the dispenser further includes a threaded locking collar around a distal portion of the nozzle. The locking collar is configured to reversibly lock together with a complementary threaded connector of a ureteroscope or ureteral catheter.

In some embodiments, the dispenser is configured to infuse the composition into the ureter through the ureteroscope or the ureteral catheter by pumping the bellows.

In some embodiments, the composition further includes a tertiary solid phase dispersed in the primary solid phase of the composition. The tertiary solid phase includes a radiopaque material configured to occupy interstices of the polymeric form upon polymerization thereof, thereby conferring radiopacity to the polymeric form.

In some embodiments, the leachable component is a salt or a sugar.

In some embodiments, the composition is configured to adhere to urothelial tissue.

Also disclosed is a packaged composition for establishing a urine passageway through a ureter. The packaged composition includes, in some embodiments, a mixing syringe including a fluid and a composition. The mixing syringe includes a mixing chamber within a primary barrel of the mixing syringe, a fluid chamber within a secondary barrel of the mixing syringe, a Luer-tapered syringe tip, and a rotatable hub including a three-way valve between the syringe tip and the primary and secondary barrels. The three-way valve is configured to fluidly connect the fluid chamber to the mixing chamber, fluidly connect the mixing chamber to a syringe-tip lumen, or close off mixing chamber, the fluid chamber, and the syringe-tip lumen from each other depending upon a degree to which the rotatable hub is rotated. The fluid is disposed in the fluid chamber, and the composition is disposed in the mixing chamber. The composition includes a primary solid phase and a secondary solid phase. The primary solid phase includes a monomer, a pre-polymer, or a mixture thereof configured to commence polymerization when contacted with the fluid. The secondary solid phase is dispersed in the primary solid phase. The secondary solid phase includes a leachable component. The leachable component is configured to leach from a polymeric form in the ureter when contacted with a sufficient amount of a same or different fluid than that of the fluid chamber. The leachable component is also configured to form pores of an open-pore network throughout the polymeric form when leached from the polymeric form, thereby establishing the urine passageway through the ureter.

In some embodiments, the mixing syringe further includes a primary plunger disposed in the primary barrel of the mixing syringe and a secondary plunger disposed in the secondary barrel of the mixing syringe. Each plunger of the primary plunger and the secondary plunger is independently actionable from the other.

In some embodiments, the mixing syringe is configured to infuse the composition dispersed or dissolved in the fluid into the ureter through a ureteroscope or a ureteral catheter by pressing the primary plunger.

In some embodiments, the mixing syringe further includes a threaded locking collar around the syringe tip. The locking collar is configured to reversibly lock together with a complementary threaded connector of a ureteroscope or ureteral catheter.

In some embodiments, the composition further includes a tertiary solid phase dispersed in the primary solid phase of the composition. The tertiary solid phase includes a radiopaque material configured to occupy interstices of the polymeric form upon polymerization thereof, thereby conferring radiopacity to the polymeric form.

In some embodiments, the leachable component is a salt or a sugar.

Also disclosed is a method for establishing a urine passageway through a ureter. The method includes, in some embodiments, a composition-infusing step, a fluid-contacting step, and a polymeric form-forming step. The composition-infusing step includes infusing a composition into the ureter through a working channel of a ureteroscope or a lumen of an open-ended ureteral catheter. The fluid-contacting step includes contacting the composition with a fluid to commence polymerization of a primary solid phase of the composition. The primary solid phase of the composition includes a monomer, a pre-polymer, or a mixture thereof. The polymeric form-forming step includes allowing a polymeric form to form in the ureter while the fluid leaches a leachable component of a secondary solid phase of the composition from the polymeric form. Leaching the leachable component of the secondary solid phase with the fluid forms pores of an open-pore network throughout the polymeric form, thereby establishing the urine passageway through the ureter.

In some embodiments, the method further includes a visualizing step. The visualizing step includes fluoroscopically visualizing the composition infusing into the ureter. The composition includes a tertiary solid phase of a radiopaque material configured to occupy interstices of the polymeric form upon formation thereof, thereby conferring radiopacity to the polymeric form.

In some embodiments, the composition-infusing step is performed before the fluid-contacting step.

In some embodiments, the method further includes a packaged composition-obtaining step, a nozzle-inserting step, and a composition-dispensing step. The packaged composition-obtaining step includes obtaining a packaged composition of the composition in a dispenser. The nozzle-inserting step includes inserting a Luer-tapered nozzle of the dispenser into a complementary connector of the ureteroscope or the ureteral catheter. The composition-dispensing step includes compressing a bellows of the dispenser to dispense a solid state of the composition, thereby infusing the composition into the ureter in accordance with the composition-infusing step.

In some embodiments, the fluid-contacting step includes dispensing saline into the ureter with a syringe or allowing urine to contact the composition in the ureter.

In some embodiments, the composition-infusing step is performed after the fluid-contacting step.

In some embodiments, the method further includes a packaged composition-obtaining step, a fluid-dispensing step, a connecting step, and a composition-dispensing step. The packaged composition-obtaining step includes obtaining a packaged composition of the composition in a mixing syringe. The fluid-dispensing step includes dispensing the fluid from a fluid chamber of the mixing syringe with a secondary plunger of the mixing syringe into a mixing chamber of the mixing syringe. The mixing chamber includes the composition. As such, the fluid-dispensing step effectuates, at least in part, the fluid-contacting step. The connecting step includes inserting a Luer-tapered syringe tip of the mixing syringe into a complementary connector of the ureteroscope or the ureteral catheter. The composition-dispensing step includes dispensing the composition dispersed or dissolved in the fluid with a primary plunger of the mixing syringe to dispense the composition, thereby infusing the composition into the ureter in accordance with the composition-infusing step.

In some embodiments, the composition-infusing step is from a kidney-end portion of the ureter to a bladder-end portion of the ureter when the infusing is performed through the ureteroscope.

In some embodiments, the composition-infusing step is from a bladder-end portion of the ureter to a kidney-end portion of the ureter when the infusing performed through the ureteral catheter.

These and other features of the concepts provided herein will become more apparent to those of skill in the art in view of the accompanying drawings and following description, which describe particular embodiments of such concepts in greater detail.

DRAWINGS

DESCRIPTION

Figure 1:
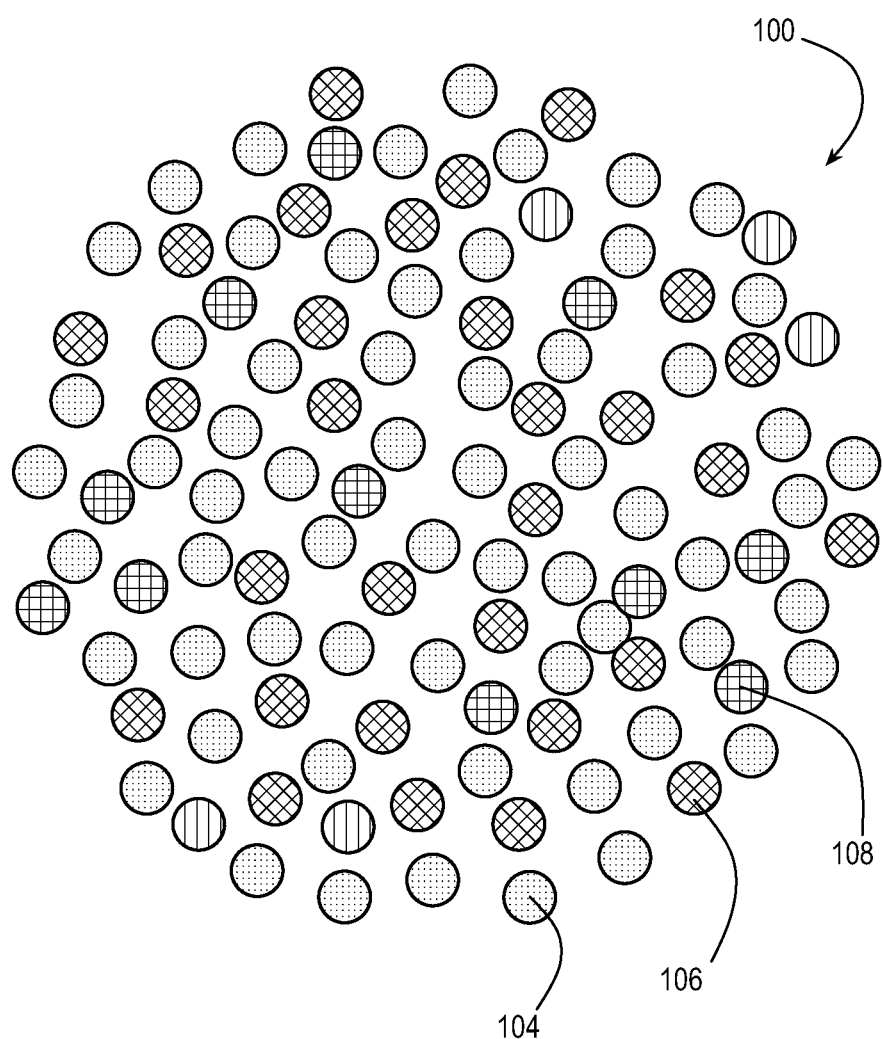
FIG. 1 illustrates a composition for establishing a urine passageway through a ureter in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

Disclosed herein are compositions, dispensers, and methods thereof for establishing a urine passageway from a kidney to a bladder through a ureter.

Compositions

Figure 2:
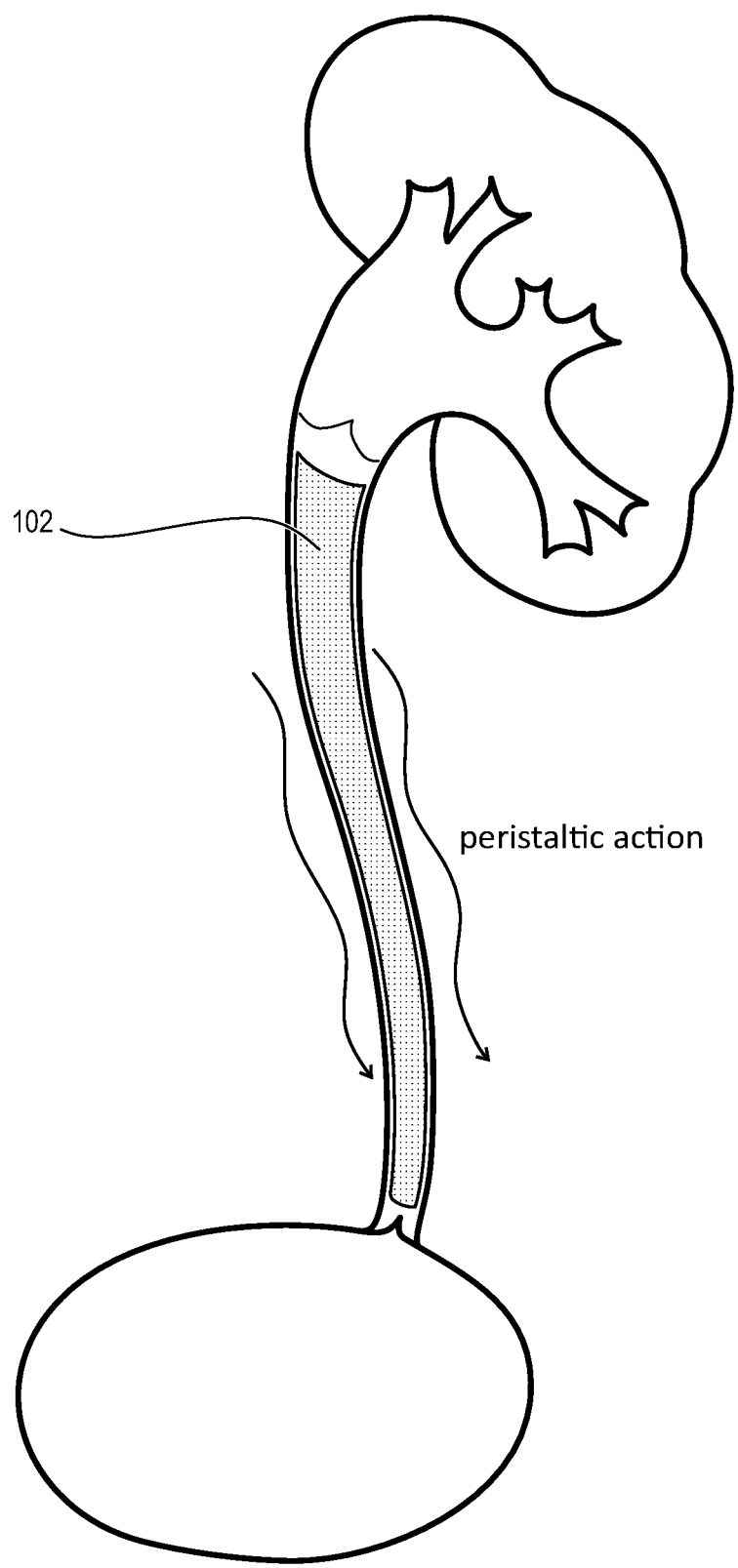
FIG. 2 illustrates a polymeric form as the urine passageway through the ureter in accordance with some embodiments.

FIG. 1 illustrates a composition 100 for establishing a urine passageway through a ureter in accordance with some embodiments. FIG. 2 illustrates a polymeric form 102 as the urine passageway through the ureter in accordance with some embodiments.

As shown, the composition 100 includes a primary solid phase 104 and a secondary solid phase 106. The secondary solid phase 106 is dispersed in the primary solid phase 104, thereby forming a heterogeneous mixture or suspension of the secondary solid phase 106 in the primary solid phase 104. The composition 100 can be a free-flowing powder configured to be infused into the ureter through a working channel of a ureteroscope or a lumen of an open-ended ureteral catheter. Such a composition is configured to adhere to at least urothelial tissue such that pigtails or the like are not needed to secure the polymeric form 102 in the ureter.

The primary solid phase 104 includes a monomer, a pre-polymer, or a mixture thereof configured to commence polymerization into the polymeric form 102 when contacted with a fluid such as urine, saline, or a mixture thereof. When polymerization occurs in the ureter, the polymeric form 102 assumes an approximate shape of the ureter.

The secondary solid phase 106 includes a leachable component such as a salt or a sugar. The leachable component is configured to leach from the polymeric form 102 when contacted with a sufficient amount of a same or different fluid than that for polymerization of the primary solid phase 104. The leachable component forms pores of an open-pore network throughout the polymeric form 102 when leached from the polymeric form 102, thereby providing a porous polymeric form 102 and establishing the urine passageway through the ureter.

The composition 100 can further include a tertiary solid phase 108 dispersed in the primary solid phase 104 of the composition 100, thereby forming a heterogeneous mixture or suspension of the secondary and tertiary solid phases 106 and 108 in the primary solid phase 104. The tertiary solid phase 108 includes a radiopaque material configured to aid visualizing infusion of the composition 100 in a ureter. In addition, the radiopaque material of the tertiary solid phase 108 is configured to occupy interstices of the polymeric form 102 upon polymerization thereof, thereby conferring radiopacity to the polymeric form 102.

As to the polymeric form 102, the polymeric form 102 assumes an approximate shape of a ureter as set forth above. In addition, the polymeric form 102 is porous, thereby allowing urine from a kidney to pass therethrough to a bladder. By way of the primary solid phase 104, the polymeric form 102 can be configured to bioabsorb over a period of time (e.g., several weeks) commensurate with an amount of the composition 100 disposed in the ureter to form the polymeric form 102. Alternatively or additionally, the polymeric form 102 can be configured to degrade in urine and flush from a urinary system over a period of time (e.g., several weeks) commensurate with an amount of the composition 100 disposed in the ureter to form the polymeric form 102. Bioabsorption or degradation of the polymeric form 102 eliminates the need of a follow-up procedure such as that needed to remove existing ureteral stents.

As set forth above, the composition 100 and, therefore, the polymeric form 102 is configured to adhere to at least urothelial tissue such that pigtails or the like of existing ureteral stents are not needed to secure the polymeric form 102 in a ureter. An absence of pigtails mitigates or eliminates bladder-wall irritation that commonly occurs with existing ureteral stents during an indwelling period thereof. In addition, the polymeric form 102 allows the one-way valve across the ureterovesicular junction to normally function. Advantageously, the polymeric form 102 can be softer and more compliant than existing ureteral stents, which reduces or eliminates interference with the peristaltic action of the smooth muscle of the ureter.

Packaged Compositions

Figure 3:
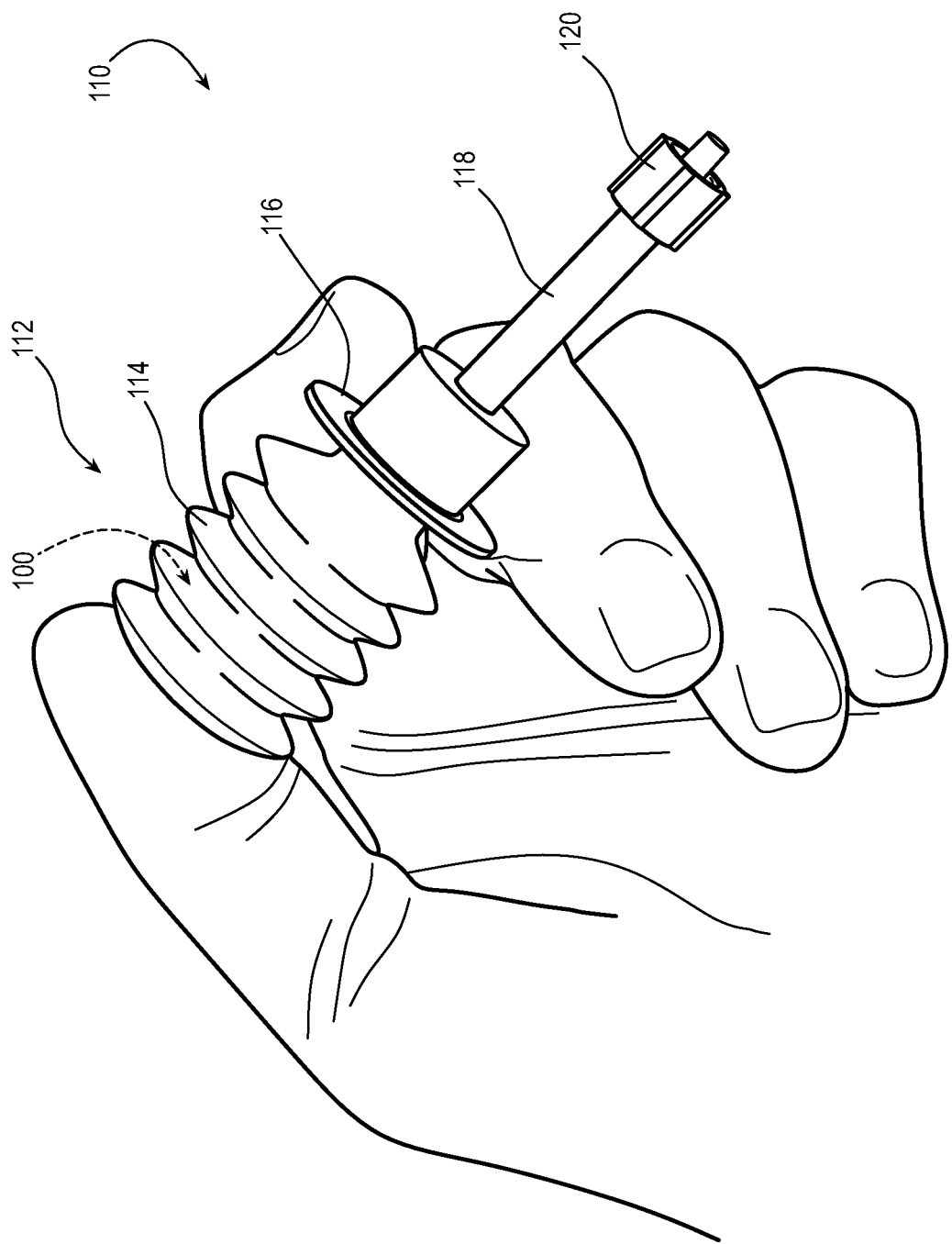
FIG. 3 illustrates a first packaged composition for establishing a urine passageway through a ureter in accordance with some embodiments.

FIG. 3 illustrates a first packaged composition 110 for establishing a urine passageway through a ureter in accordance with some embodiments.

As shown, the packaged composition 110 includes a dispenser 112 including the composition 100. The dispenser 112 is configured to infuse the composition 100 into a ureter through a ureteroscope or a ureteral catheter.

The dispenser 112 includes a bellows 114 coupled to a flanged hub 116 having a Luer-tapered nozzle 118. The bellows 114 includes the composition 100 disposed therein. Indeed, the dispenser 112 is configured to infuse the composition 100 into a ureter through a ureteroscope or a ureteral catheter by pumping the bellows 114. Pumping the bellows 114 includes iteratively compressing the bellows 114 to dispense the composition 100 and allowing the bellows 114 to expand to an equilibrium state thereof.

While not shown, the dispenser 112 further includes a valve fluidly connected to the bellows 114. The valve is configured to open and provide air to the bellows 114 when the bellows 114 are allowed to return to the equilibrium state thereof.

The dispenser 112 can further include a threaded locking collar 120 around a distal portion of the nozzle 118 as shown. Such a locking collar is configured to reversibly lock together with a complementary threaded connector of a ureteroscope or ureteral catheter.

Figure 4:
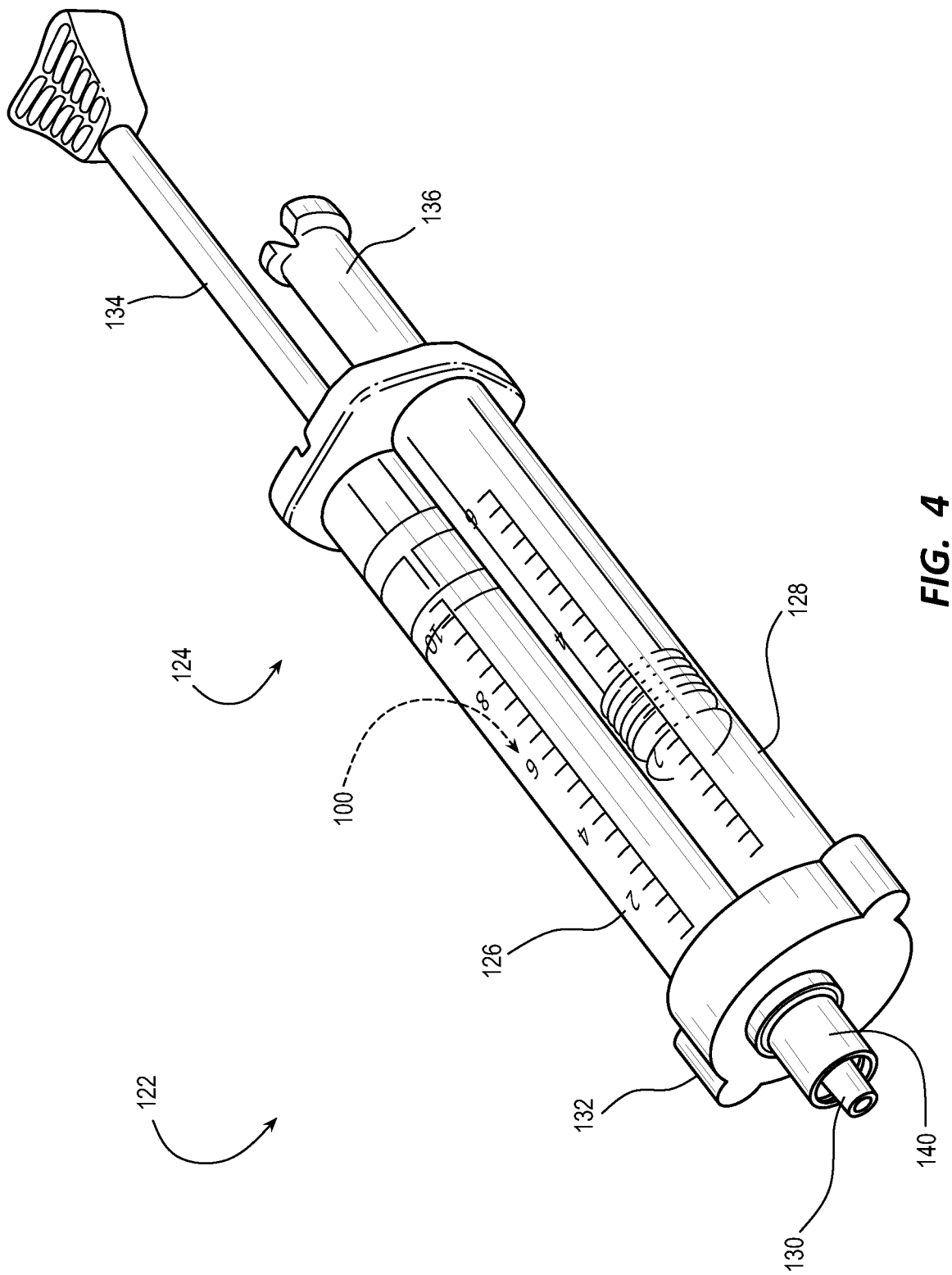
FIG. 4 illustrates a second packaged composition for establishing a urine passageway through a ureter in accordance with some embodiments.
Figure 5:
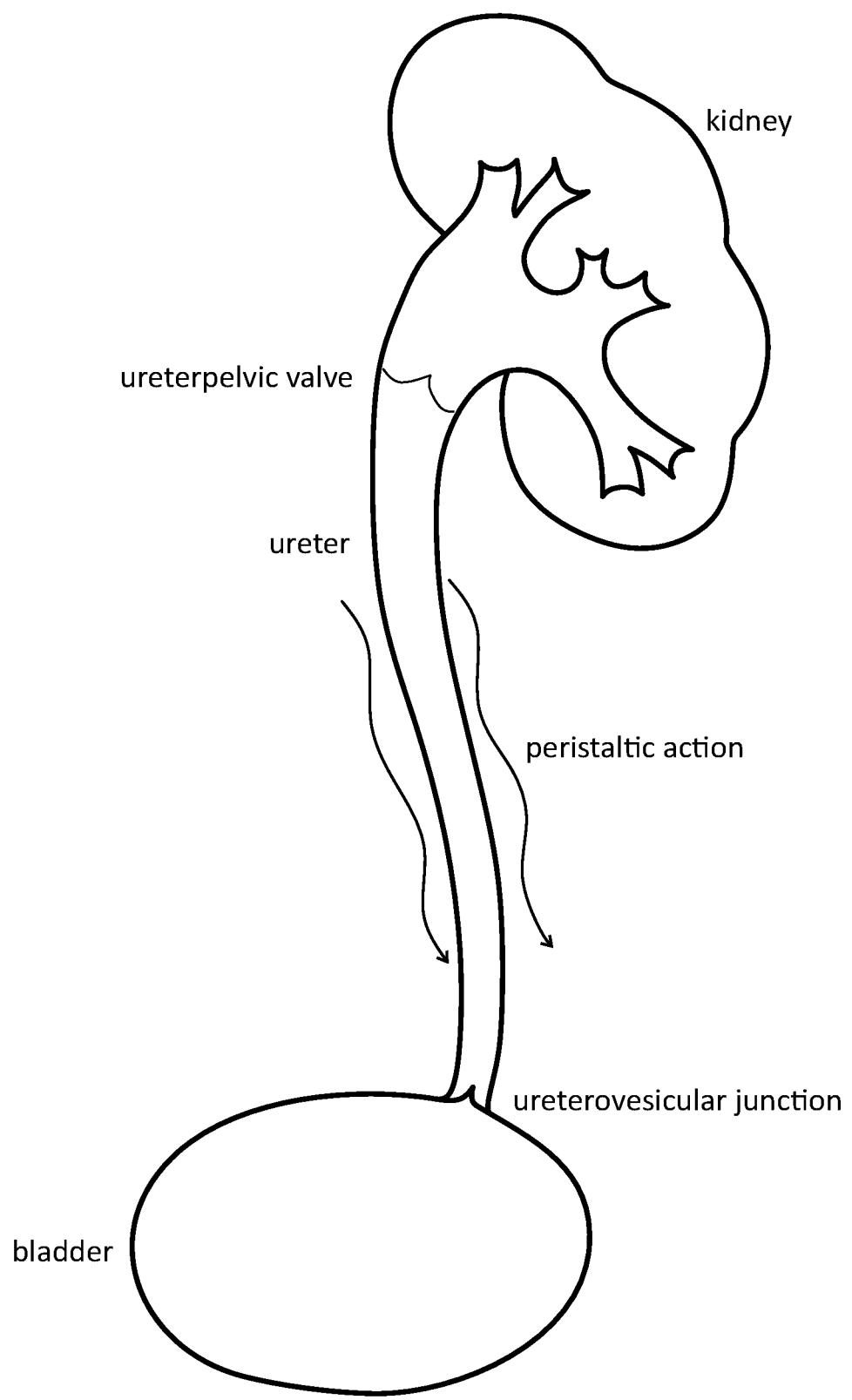
FIG. 5 illustrates a portion of a urinary system including a kidney, a bladder, a ureter between the kidney and the bladder, a ureteropelvic valve between the kidney and the ureter, and a ureterovesicular junction between the bladder and the ureter.
Figure 6:
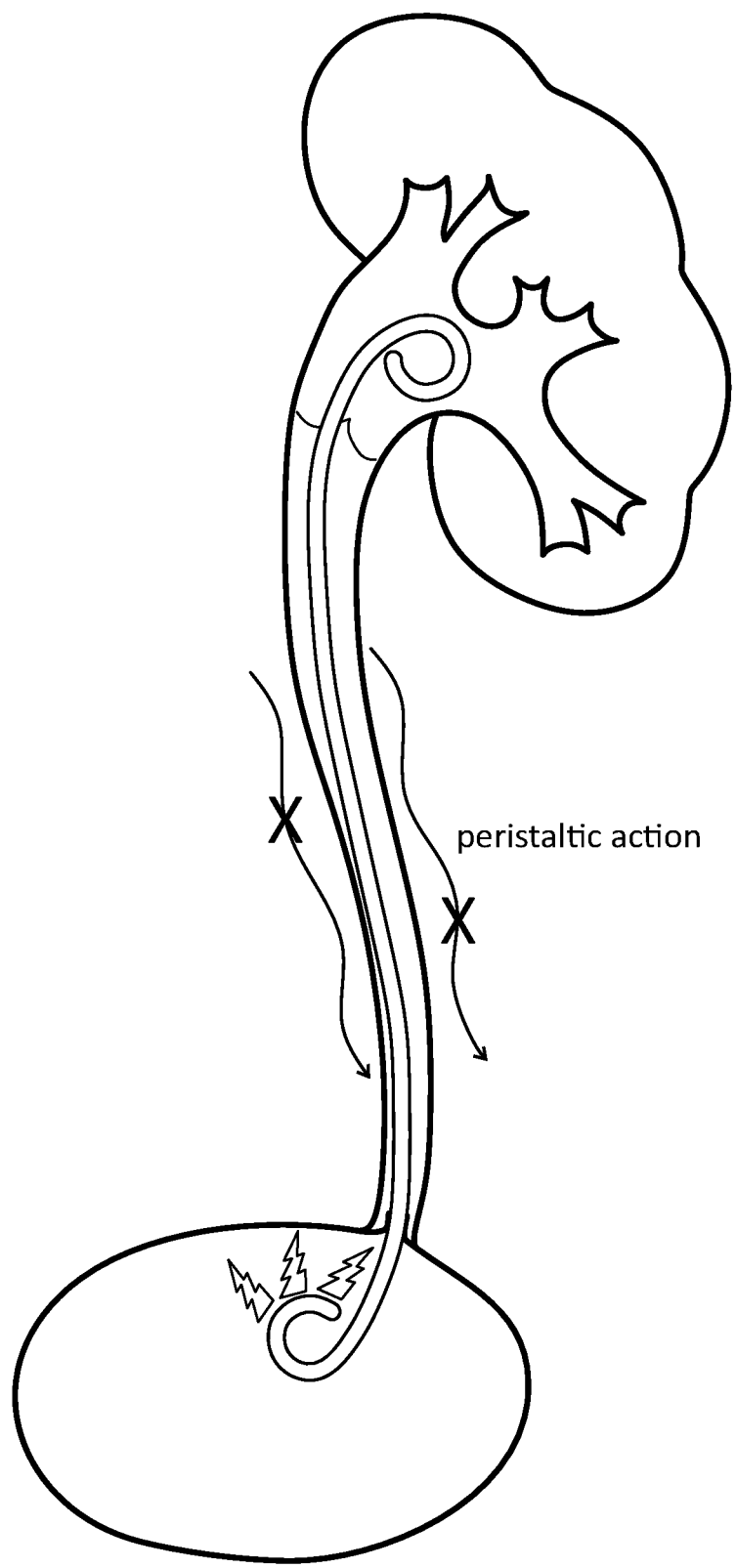
FIG. 6 illustrates a conventional pigtailed ureteral stent disposed in a ureter with pigtails disposed in the kidney and the bladder.

FIG. 4 illustrates a second packaged composition 122 for establishing a urine passageway through a ureter in accordance with some embodiments.

As shown, the packaged composition 122 includes a mixing syringe 124 including a fluid and the composition 100, the mixing syringe 124 configured as both a mixer and dispenser for the composition 100. Indeed, the mixing syringe 124 is configured to mix and infuse the composition 100 dispersed or dissolved in the fluid into the ureter through a ureteroscope or a ureteral catheter.

The mixing syringe 124 includes a mixing chamber within a primary barrel 126 of the mixing syringe 124, a fluid chamber within a secondary barrel 128 of the mixing syringe 124, a Luer-tapered syringe tip 130, and a rotatable hub 132 including a three-way valve between the syringe tip 130 and the primary and secondary barrels 126 and 128. The fluid is disposed in the fluid chamber, and the composition 100 is disposed in the mixing chamber.

The three-way valve is configured to fluidly connect the fluid chamber to the mixing chamber, fluidly connect the mixing chamber to a syringe-tip lumen, or close off the mixing chamber, the fluid chamber, and the syringe-tip lumen from each other depending upon a degree to which the rotatable hub 132 is rotated. Fluidly connecting the fluid chamber to the mixing chamber allows the fluid in the fluid chamber to be dispensed into the mixing chamber for contacting the composition 100 with the fluid to commence polymerization of the primary solid phase 104 of the composition 100. Fluidly connecting the mixing chamber to the syringe-tip lumen allows the composition 100 dispersed or dissolved in the fluid to be dispensed into a ureter to complete polymerization of the primary solid phase 104 of the composition 100.

The mixing syringe 124 further includes a primary plunger 134 disposed in the primary barrel 126 of the mixing syringe 124 and a secondary plunger 136 disposed in the secondary barrel 128 of the mixing syringe 124. Each plunger of the primary plunger 134 and the secondary plunger 136 is independently actionable from the other. Indeed, the secondary plunger 136 is independently actionable for dispensing the fluid from the fluid chamber of the mixing syringe 124 into the mixing chamber of the mixing syringe 124 by pressing the secondary plunger 136. And the primary plunger 134 is independently actionable for dispensing the composition 100 dispersed or dissolved in the fluid into the ureter through a ureteroscope or a ureteral catheter by pressing the primary plunger 134.

The mixing syringe 124 can further include a threaded locking collar 140 around the syringe tip 130 as shown. Such a locking collar is configured to reversibly lock together with a complementary threaded connector of a ureteroscope or ureteral catheter.

Methods

Methods include a method for establishing a urine passageway through a ureter. Such a method can generally include a composition-infusing step, a fluid-contacting step, and a polymeric form-forming step.

The composition-infusing step includes infusing the composition 100 into the ureter through a working channel of a ureteroscope or a lumen of an open-ended ureteral catheter. Depending upon the procedure under which the composition-infusing step occurs, the composition-infusing step can be performed in one of two directions. In an example, the composition-infusing step can be performed from a kidney-end portion of the ureter to a bladder-end portion of the ureter when the composition-infusing step is performed through the ureteroscope. In another example, the composition-infusing step can be performed from a bladder-end portion of the ureter to a kidney-end portion of the ureter when the composition-infusing step is performed through the ureteral catheter (e.g., in a PCNL procedure).

The fluid-contacting step includes contacting the composition 100 with a fluid to commence polymerization of the primary solid phase 104 of the composition 100. As set forth above, the primary solid phase 104 of the composition 100 includes a monomer, a pre-polymer, or a mixture thereof. As set forth below, the fluid-contacting step can take place in the ureter or the mixing syringe 124.

The polymeric form-forming step includes allowing the polymeric form 102 to form in the ureter while the fluid leaches the leachable component of the secondary solid phase 106 of the composition 100 from the polymeric form 102. Leaching the leachable component of the secondary solid phase 106 with the fluid forms pores of an open-pore network throughout the polymeric form 102, thereby establishing the urine passageway through the ureter.

The method can further include a visualizing step, particularly if the composition-infusing step is not directly visualized by way of the ureteroscope. The visualizing step includes fluoroscopically visualizing the composition 100 infusing into the ureter. Again, the composition 100 can include the tertiary solid phase 108 of a radiopaque material configured to aid visualizing the composition 100 infusing into the ureter. In addition, the radiopaque material occupies interstices of the polymeric form 102 upon formation thereof, thereby conferring radiopacity to the polymeric form 102.

The foregoing general method can be modified in accordance with a chosen dispenser for dispensing the composition 100. For example, the foregoing composition-infusing step can be performed before the fluid-contacting step when using the dispenser 112.

In view of the foregoing, the method can further include a packaged composition-obtaining step, a nozzle-inserting step, and a composition-dispensing step.

The packaged composition-obtaining step includes obtaining the packaged composition 110 of the composition 100 in the dispenser 112.

The nozzle-inserting step includes inserting the Luer-tapered nozzle 118 of the dispenser 112 into a complementary connector of the ureteroscope or the ureteral catheter.

The composition-dispensing step includes compressing the bellows 114 of the dispenser 112 to dispense a solid state of the composition 100, thereby infusing the composition 100 into the ureter in accordance with the composition-infusing step.

The fluid-contacting step thusly includes dispensing saline into the ureter with a syringe or allowing urine to contact the composition 100 in the ureter.

Again, the foregoing general method can be modified in accordance with a chosen dispenser for dispensing the composition 100. For example, the foregoing composition-infusing step can be performed after the fluid-contacting step when using the mixing syringe 124.

In view of the foregoing, the method can further include a packaged composition-obtaining step, a fluid-dispensing step, a connecting step, and a composition-dispensing step.

The packaged composition-obtaining step includes obtaining the packaged composition 122 of the composition 100 in the mixing syringe 124.

The fluid-dispensing step thusly includes dispensing the fluid from the fluid chamber of the mixing syringe 124 with the secondary plunger 136 of the mixing syringe 124 into the mixing chamber of the mixing syringe 124. The mixing chamber includes the composition 100. As such, the fluid-dispensing step effectuates, at least in part, the fluid-contacting step.

The connecting step includes inserting the Luer-tapered syringe tip 130 of the mixing syringe 124 into a complementary connector of the ureteroscope or the ureteral catheter.

The composition-dispensing step includes dispensing the composition 100 dispersed or dissolved in the fluid with the primary plunger 134 of the mixing syringe 124 to dispense the composition 100, thereby infusing the composition 100 into the ureter in accordance with the composition-infusing step.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A packaged composition for establishing a urine passageway through a ureter, comprising:
    a mixing syringe including:
        a mixing chamber within a primary barrel of the mixing syringe;
        a fluid chamber within a secondary barrel of the mixing syringe;
        a Luer-tapered syringe tip; and
        a rotatable hub including a three-way valve between the Luer-tapered syringe tip and the primary and secondary barrels, the three-way valve configured to fluidly connect the fluid chamber to the mixing chamber, fluidly connect the mixing chamber to a syringe-tip lumen, or close off the mixing chamber, the fluid chamber, and the syringe-tip lumen from each other depending upon a degree to which the rotatable hub is rotated;
    a fluid disposed in the fluid chamber; and
    a composition disposed in the mixing chamber, the composition including:
        a primary solid phase of a monomer, a pre-polymer, or a mixture thereof configured to commence polymerization when contacted with the fluid; and
        a secondary solid phase dispersed in the primary solid phase including a leachable component, the leachable component configured to leach from a polymeric form in the ureter when contacted with a sufficient amount of a same or different fluid and form pores of an open-pore network throughout the polymeric form, thereby establishing the urine passageway through the ureter.

2. The packaged composition of claim 1, the mixing syringe further comprising:
    a primary plunger disposed in the primary barrel of the mixing syringe; and
    a secondary plunger disposed in the secondary barrel of the mixing syringe, the primary plunger and the secondary plunger independently actionable from each other.

3. The packaged composition of claim 2, wherein the mixing syringe is configured to infuse the composition dispersed or dissolved in the fluid into the ureter through a ureteroscope or a ureteral catheter by pressing the primary plunger.

4. The packaged composition of claim 3, the mixing syringe further comprising:
    a threaded locking collar around the Luer-tapered syringe tip, the threaded locking collar configured to reversibly lock together with a complementary threaded connector of the ureteroscope or the ureteral catheter.

5. The packaged composition of claim 1, the composition further comprising:
    a tertiary solid phase dispersed in the primary solid phase of the composition, the tertiary solid phase including a radiopaque material configured to occupy interstices of the polymeric form upon polymerization thereof, thereby conferring radiopacity to the polymeric form.

6. The packaged composition of claim 1, wherein the leachable component is a salt or a sugar.

7. A method for establishing a urine passageway through a ureter, comprising:
    obtaining a packaged composition of a composition in a mixing syringe, the mixing syringe including:
        a mixing chamber within a primary barrel of the mixing syringe;

a fluid chamber within a secondary barrel of the mixing syringe;
a Luer-tapered syringe tip; and
a rotatable hub including a three-way valve between the Luer-tapered syringe tip and the primary and secondary barrels, the three-way valve configured to fluidly connect the fluid chamber to the mixing chamber, fluidly connect the mixing chamber to a syringe-tip lumen, or close off the mixing chamber, the fluid chamber, and the syringe-tip lumen from each other depending upon a degree to which the rotatable hub is rotated;
infusing the composition into the ureter through a working channel of a ureteroscope or a lumen of an open-ended ureteral catheter;
contacting the composition with a fluid to commence polymerization of a primary solid phase of the composition including a monomer, a pre-polymer, or a mixture thereof; and
allowing a polymeric form to form the ureter while the fluid leaches a leachable component of a secondary solid phase of the composition from the polymeric form, thereby forming pores of an open-pore network throughout the polymeric form and establishing the urine passageway through the ureter.

8. The method of claim 7, further comprising:
fluoroscopically visualizing the infusing of the composition into the ureter, the composition including a tertiary solid phase of a radiopaque material configured to occupy interstices of the polymeric form upon formation thereof, thereby also conferring radiopacity to the polymeric form.

9. The method of claim 7, wherein the infusing of the composition into the ureter is performed before the contacting of the composition with the fluid to commence polymerization.

10. The method of claim 7, wherein the infusing of the composition into the ureter is performed after the contacting of the composition with the fluid to commence polymerization.

11. The method of claim 10, further comprising:
dispensing the fluid from the fluid chamber of the mixing syringe with a second plunger of the mixing syringe into the mixing chamber of the mixing syringe, the mixing chamber including the composition, thereby contacting the composition with the fluid to commence polymerization;
inserting the Luer-tapered syringe tip of the mixing syringe into a complementary connector of the ureteroscope or the open-ended ureteral catheter; and
dispensing the composition dispersed or dissolved in the fluid with a first plunger of the mixing syringe to dispense the composition, thereby infusing the composition into the ureter through the ureteroscope or the open-ended ureteral catheter.

12. The method of claim 7, wherein the infusing of the composition is from a kidney-end portion of the ureter to a bladder-end portion of the ureter, the infusing performed through the ureteroscope.

13. The method of claim 7, wherein the infusing of the composition is from a bladder-end portion of the ureter to a kidney-end portion of the ureter, the infusing performed through the open-ended ureteral catheter.

\* \* \* \* \*